(12) United States Patent
Banerjee et al.

(10) Patent No.: US 11,880,962 B2
(45) Date of Patent: Jan. 23, 2024

(54) SYSTEM AND METHOD FOR SYNTHESIZING MAGNETIC RESONANCE IMAGES

(71) Applicants: General Electric Company, Schenectady, NY (US); THE BOARD OF TRUSTEES OF THE LELAND STANFORD JUNIOR UNIVERSITY, Stanford, CA (US)

(72) Inventors: Suchandrima Banerjee, Menlo Park, CA (US); Enhao Gong, Palo Alto, CA (US); Greg Zaharchuk, Palo Alto, CA (US); John M. Pauly, Palo Alto, CA (US)

(73) Assignees: GENERAL ELECTRIC COMPANY, Schenectady, NY (US); THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 59 days.

(21) Appl. No.: 16/966,125

(22) PCT Filed: Feb. 14, 2019

(86) PCT No.: PCT/US2019/017993
§ 371 (c)(1),
(2) Date: Jul. 30, 2020

(87) PCT Pub. No.: WO2019/161043
PCT Pub. Date: Aug. 22, 2019

(65) Prior Publication Data
US 2021/0027436 A1 Jan. 28, 2021

Related U.S. Application Data

(60) Provisional application No. 62/631,102, filed on Feb. 15, 2018.

(51) Int. Cl.
*G06T 5/00* (2006.01)
*A61B 5/055* (2006.01)
(Continued)

(52) U.S. Cl.
CPC .............. *G06T 5/009* (2013.01); *A61B 5/055* (2013.01); *G06T 5/50* (2013.01); *G06T 7/0012* (2013.01);
(Continued)

(58) Field of Classification Search
CPC ......... G06T 5/009; G06T 5/50; G06T 7/0012; G06T 2207/10088; G06T 2207/20081;
(Continued)

(56) References Cited

U.S. PATENT DOCUMENTS

2010/0103166 A1* 4/2010 Warntjes ................ A61B 5/055
345/617
2010/0296717 A1* 11/2010 Takizawa ........... G01R 33/5617
382/131
(Continued)

FOREIGN PATENT DOCUMENTS

CN 107194933 A 9/2017
WO 2017-165801 A1 9/2017

OTHER PUBLICATIONS

Xiao Han: "MR-based synthetic CT generation using a deep convolutional neural network method", Medical Physics, vol. 44, No. 4, Apr. 2017 (Apr. 1, 2017), pp. 1408-1419, XP055636079 (Year: 2017).*

(Continued)

*Primary Examiner* — Van D Huynh

(57) ABSTRACT

Methods and systems for synthesizing contrast images from a quantitative acquisition are disclosed. An exemplary method includes performing a quantification scan, using a trained deep neural network to synthesize a contrast image
(Continued)

from the quantification scan, and outputting the contrast image synthesized by the trained deep neural network. In another exemplary method, an operator can identify a target contrast type for the synthesized contrast image. A trained discriminator and classifier module determines whether the synthesized contrast image is of realistic image quality and whether the synthesized contrast image matches the target contrast type.

18 Claims, 8 Drawing Sheets

(51) Int. Cl.
  *G06T 5/50*   (2006.01)
  *G06T 7/00*   (2017.01)
(52) U.S. Cl.
  CPC .............. *G06T 2207/10088* (2013.01); *G06T 2207/20081* (2013.01); *G06T 2207/20084* (2013.01)
(58) Field of Classification Search
  CPC . G06T 2207/20084; A61B 5/055; A61B 5/00; G06N 3/08
  USPC .......................................................... 382/131
  See application file for complete search history.

(56) References Cited

U.S. PATENT DOCUMENTS

| | | | |
|---|---|---|---|
| 2011/0018537 A1* | 1/2011 | Warntjes ............ | G01R 33/5602 324/309 |
| 2017/0035321 A1 | 2/2017 | Polimeni | |
| 2019/0035078 A1* | 1/2019 | Zaharchuk ................ | G06T 5/20 |
| 2019/0049540 A1* | 2/2019 | Odry ..................... | G01R 33/543 |
| 2019/0108634 A1* | 4/2019 | Zaharchuk ................ | G06T 3/60 |
| 2019/0362522 A1* | 11/2019 | Han ..................... | A61N 5/1039 |

OTHER PUBLICATIONS

Hagiwara A, Hori M, Suzuki M, et al. "Contrast-enhanced synthetic MRI for the detection of brain metastases". Acta Radiologica Open. Feb. 2016. doi:10.1177/2058460115626757 (Year: 2016).*
Mika Kapanen et al.: "T1/T2*-weighted MRI provides clinically relevant pseudo-CT density data for the pelvic bones in MRI-only based radiotherapy treatment planning", Acta Oncologica, vol. 52, Jun. 19, 2012 (Jun. 19, 2012), pp. 612-618, XP055283512 (Year: 2012).*
L.N. Tanenbaum et al.: "Synthetic MRI for Clinical Neuroimaging: Results of the Magnetic Resonance Image Compilation (MAGiC) Prospective, Multicenter, Multireader Trial", American Journal of Neuroradiology, vol. 38, Apr. 2017 (Apr. 1, 2017), pp. 1103-1110, XP055630060 (Year: 2017).*
Han, X., "MR-based synthetic CT generation using a deep convolutional neural network method," Medical Physics, first published Feb. 13, 2017, DOI: 10.1002/mp.12155, vol. 44, No. 4, Retrieved from the Internet URL: http://pdf.xuebalib.com:1262/xuebalib.com.38052.pdf on Jul. 14, 2020, believed same as Examiner's retrieval from the Internet at https://aapm.onlinelibrary.wiley.com/doi/abs/10.1002/mp.12155 on May 22, 2019, pp. 1408-1419.
Tanenbaum, L.N. et al., "Synthetic MRI for Clinical Neuroimaging: Results of the MAGnetic resonance Image Compilation (MAGiC) Prospective, Multi-center, Multi-reader Trial," American Journal of Neuroradiology, published Apr. 27, 2017, DOI: 10.3174/ajnr.a5227, Retrieved from the Internet URL: https://www.researchgate.net/publication/314392721, pp. 1-9.
Kapanen, M. et al., "T1/T2*-weighted MRI provides clinically relevant pseudo-CT density data for the pelvic bones in MRI-only based radiotherapy treatment planning," Acta Oncologica, Published online: Jun. 19, 2012, DOI: 10.3109/0284186X.2012.692883, Retrieved from the Internet URL: https://doi.org/10.3109/0284186X.2012.692883, pp. 612-618.
International Search Report of the International Searching Authority for PCT/US2019/017993 dated May 28, 2019.
CN application 201980010251.9 national filed Jul. 27, 2020—Office Action dated Mar. 16, 2023; 38 pages.

* cited by examiner

SYSTEM AND METHOD FOR SYNTHESIZING MAGNETIC RESONANCE IMAGES

CROSS REFERENCE

This application claims priority to U.S. Provisional Application No. 62/631,102, filed Feb. 15, 2018, which is incorporated herein by reference in its entirety.

TECHNICAL FIELD

The present disclosure relates generally to magnetic resonance imaging (MRI), and more specifically, to synthetic MRI using a deep learning approach.

BACKGROUND

MRI is a widely accepted and commercially available imaging modality for obtaining medical images of the interior of a patient based on magnetism of the nucleus. Various tissues, such as water-based tissues, fat-based tissues, and fluids, in a human body can have different signal intensities on magnetic resonance (MR) images due to differences in MR properties. The differences are described as image contrasts. MRI can produce a wide range of contrasts by emphasizing a particular MR property while minimizing the others. For example, a proton density-weighted image emphasizes the difference in spin density of various tissues/fluids being analyzed. A T1-weighted image emphasizes the difference in relaxation time for the recovery of magnetization along the longitudinal direction. A T2-weighted image emphasizes the difference in relaxation time for the recovery of magnetization along the transverse direction. A short TI inversion recovery (STIR) image suppresses signals from fat. A fluid attenuated inversion recovery (FLAIR) image suppresses signals from fluid, and so on.

Different contrasts can be produced by using different pulse sequences and choosing appropriate pulse sequence parameters. For example, a T1-weighted image can be produced by spin echo (SE) sequences or gradient echo (GRE) sequences with short echo time (TE) and short repetition time (TR). A T2-weighted image can be generated by using SE or GRE sequences with long TE and long TR. In many medical examinations, different image contrasts are needed for diagnosis, which are acquired by performing several scans with different pulse sequences and parameters.

To reduce scanning time, a technology called synthetic MRI has been developed which can reconstruct multiple image contrasts with a single scan. With synthetic MRI, T1- and T2-weighted, T1- and T2-FLAIR, STIR, and/or proton density-weighted images can be produced from signals acquired in one scan in far less the total time it would take to acquire each contrast separately. Generally speaking, synthetic MRI uses a multi-delay multi-echo (MDME) sequence which includes interleaved slice-selective radio frequency (RF) pulse and multi-echo acquisition. This sequence is repeated with different delays between the RF pulse and the acquisition. MR signals acquired with MDME sequences are used to compute parameter maps (e.g., T1 map, T2 map, and proton density map, etc.) based on a pre-defined model which describes MR signal behavior pixel by pixel (or voxel by voxel). The parameter maps and operator-specified parameters (e.g., TE, TR, delay) are then used to create a "synthesized" image based on the model pixel by pixel (or voxel by voxel). The synthesized image is comparable to what would have been formed by using the operator-specified parameters in an actual MR scan.

Clinical studies have shown the applicability of synthetic MRI for brain scans. However, the pixel-wise (or voxel-wise) model-fitting method as described above may result in inaccurate parameter estimation and undesired artifacts because the model-fitting method tries to achieve a closest fitting of parameters which may lead to artifacts and errors in the synthesized images due to nonlinear nonlocal transform. For example, as shown in clinical studies, sequence-specific artifacts such as incomplete cerebrospinal fluid (CSF) suppression and pseudo-edge enhancement are more pronounced in synthesized T2-FLAIR images. In addition, the model-fitting method cannot be used to synthesize certain image contrasts such as T2*-weighted image, which reflects susceptibility differences in tissues. Improvements to synthetic MRI are generally desired.

SUMMARY

In one embodiment, the present disclosure provides a method for synthesizing an MR contrast image. The method comprises performing a quantification scan, using a trained deep neural network to synthesize a contrast image from a quantitative acquisition obtained by the quantification scan, and outputting the contrast image synthesized by the trained deep neural network.

In another embodiment, the present disclosure provides an MRI system. The MRI system comprise a gradient coil assembly configured to generate gradient magnetic fields, a radio frequency (RF) coil assembly configured to generate RF pulses, a display, and a controller in communication with the gradient coil assembly, the RF coil assembly, and the display. The controller is configured to instruct the gradient coil assembly and RF assembly to generate a sequence perform a quantification scan, instruct a trained deep neural network to synthesize a contrast image from a quantitative acquisition obtained by the quantification scan, and output the contrast image synthesized by the trained deep neural network at the display.

In yet another embodiment, the present disclosure provides a method for method for synthesizing an MR contrast image. The method comprises performing a quantification scan, receiving a target contrast type identified by an operator, and using a trained deep neural network to synthesize a contrast image from a quantitative acquisition obtained by the quantification scan based on the target contrast type. The method also comprises using a trained discriminator to determine whether the synthesized contrast image is of realistic image quality, and in response to determining that the synthesized contrast image is of realistic image quality, using a trained classifier to determine the contrast type of the synthesized contrast image, determining whether the determined contrast type matches the target contrast type, and in response to determining that the determined contrast type matches the target contrast type, outputting the synthesized image.

BRIEF DESCRIPTION OF THE DRAWINGS

Various aspects of this disclosure may be better understood upon reading the following detailed description and upon reference to the drawings in which.

Figure 1:
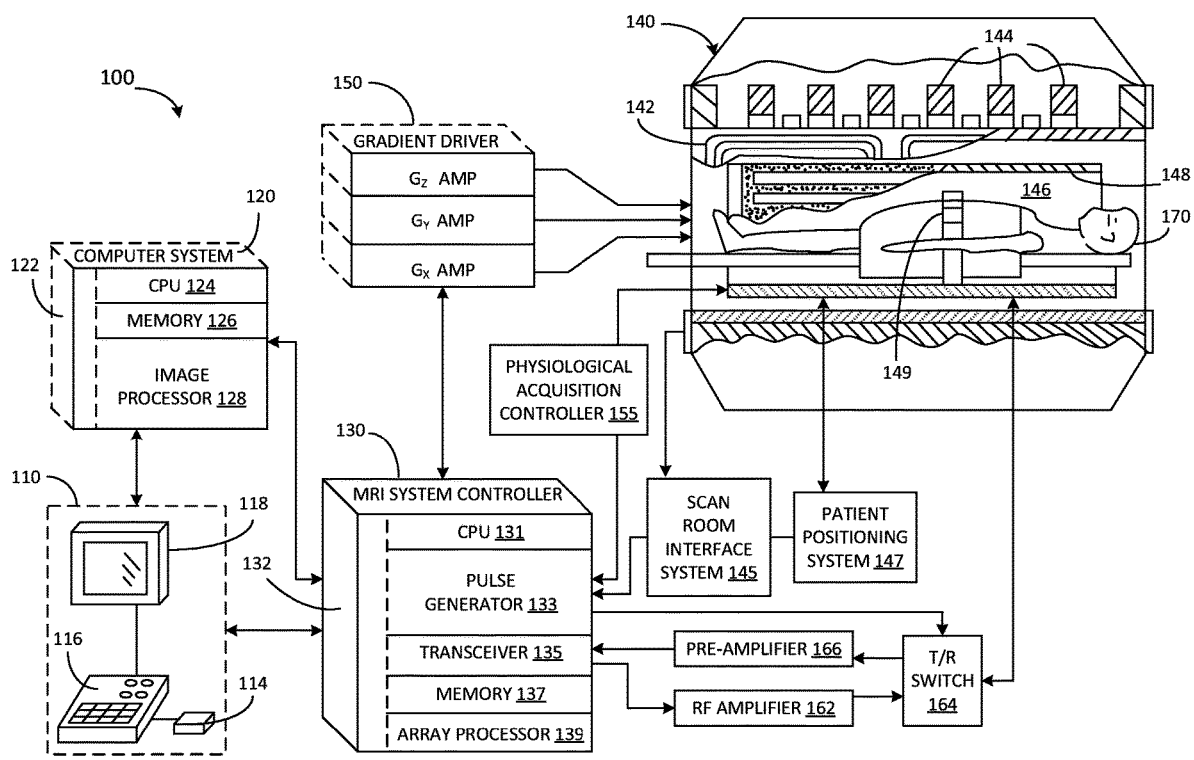
FIG. 1 is a schematic diagram of an MRI system, in accordance with an exemplary embodiment.

The drawings illustrate specific aspects of the described components, systems and methods for synthesizing MR images using a deep learning approach. Together with the following description, the drawings demonstrate and explain the principles of the structures, methods, and principles described herein. In the drawings, the thickness and size of components may be exaggerated or otherwise modified for clarity. Well-known structures, materials, or operations are not shown or described in detail to avoid obscuring aspects of the described components, systems and methods.

DETAILED DESCRIPTION

One or more specific embodiments of the present disclosure are described below in order to provide a thorough understanding. These described embodiments are only examples of the systems and methods for synthesizing contrast MR images from a quantification scan using a deep learning approach. The skilled artisan will understand that specific details described in the embodiments can be modified when being placed into practice without deviating the spirit of the present disclosure.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

Referring to the figures generally, the present disclosure is related to synthetic MRI. Synthetic MRI can reconstruct multiple image contrasts (e.g., T1- and T2-weighted, T1- and T2-FLAIR, proton density-weighted, STIR images) from MR signals acquired with a quantification sequence (e.g., MDME sequences) in a single scan. Conventionally, a pre-defined model describing MR signal behavior is used to compute parameter maps (e.g., T1, T2, and proton density maps) from the acquired MR signals pixel by pixel (or voxel by voxel). Then various image contrasts are produced by synthesizing the parameter maps and operator-specified parameters (e.g., TE, TR, delay) based on the model pixel by pixel (or voxel by voxel). However, the pixel-wise (or voxel-wise) model-fitting method does not produce satisfying results for some image contrast (e.g., T2-FLAIR), and furthermore, cannot be used to synthesize certain image contrast (e.g., T2*-weighted image).

The present disclosure uses a deep learning based approach for synthesizing MRI contrasts. In particular, a deep learning model (e.g., deep neural network) is trained by a plurality of datasets, each dataset including one or more ground truth images each acquired by a contrast scan and a corresponding acquisition by a quantification scan. As used herein, a "contrast scan" refers to the measurement of MR signals reflecting difference (i.e., contrast) in physical parameters of tissues being scanned. In an image acquired by a contrast scan, the absolute signal intensity has no direct meaning; it is rather the intensity difference that leads to a diagnosis. Contrast images are produced directly from contrast scans, for example, T1- and T2-weighted images, T1- and T2-FLAIR images, proton density-weighted images, STIR images, etc. are contrast images. As used herein, a "quantification scan" refers to the measurement of MR signals reflecting absolute values of physical parameters of tissues being scanned. The deep learning model is trained to map the acquisition by a quantification scan to the corresponding one or more contrast images. "Acquisition by a quantification scan" is also referred to as "quantitative acquisition" in this disclosure. The trained (and validated) deep learning model is then applied to a new quantitative acquisition to synthesize one or more contrast images. The deep learning based approach is shown to outperform the conventional model-fitting method with improved synthesis accuracy and reduced artifacts. Furthermore, the deep learning based approach is capable of synthesizing certain image contrast (e.g., T2*-weighted image) which cannot be produced by the conventional method.

In some embodiments, the deep learning model is trained in an intra-contrast manner. For example, one model is dedicated to a particular contrast type or a separate channel is set up for each contrast type within a model, each model or channel being trained separately. In some embodiments, the deep learning model is trained in an inter-contrast manner. For example, one set of network parameters (e.g., weights and biases) is trained and used for multiple contrast types. Correlation between different contrast types is utilized to reach a mutual correction effect.

Referring to FIG. 1, a schematic diagram of an exemplary MRI system 100 is shown in accordance with an embodiment. The operation of MRI system 100 is controlled from an operator workstation 110 that includes an input device 114, a control panel 116, and a display 118. The operator workstation 110 is coupled to and communicates with a computer system 120 that enables an operator to control the production and viewing of images on display 118. The computer system 120 includes a plurality of components that communicate with each other via electrical and/or data connections 122. The components of the computer system 120 include a central processing unit (CPU) 124, a memory 126, which may include a frame buffer for storing image data, and an image processor 128. In an alternative embodiment, the image processor 128 may be replaced by image processing functionality implemented in the CPU 124. The computer system 120 may be connected to archival media devices, permanent or back-up memory storage, or a network. The computer system 120 is coupled to and communicates with a separate MRI system controller 130.

The MRI system controller 130 includes a set of components in communication with each other via electrical and/or data connections 132. The components of the MRI system controller 130 include a CPU 131, a pulse generator 133, which is coupled to and communicates with the operator workstation 110, a transceiver 135, a memory 137, and an array processor 139. In an alternative embodiment, the pulse generator 133 may be integrated into a resonance assembly 140 of the MRI system 100. The MRI system controller 130 is coupled to and receives commands from the operator workstation 110 to indicate the MRI scan sequence to be performed during a MRI scan. The MRI system controller 130 is also coupled to and communicates with a gradient driver system 150, which is coupled to a gradient coil assembly 142 to produce magnetic field gradients during a MRI scan.

The pulse generator 133 may also receive data from a physiological acquisition controller 155 that receives signals from a plurality of different sensors connected to an object or patient 170 undergoing a MRI scan, such as electrocardiography (ECG) signals from electrodes attached to the patient. And finally, the pulse generator 133 is coupled to and communicates with a scan room interface system 145, which receives signals from various sensors associated with the condition of the resonance assembly 140. The scan room interface system 145 is also coupled to and communicates with a patient positioning system 147, which sends and receives signals to control movement of a patient table to a desired position for a MRI scan.

The MRI system controller 130 provides gradient waveforms to the gradient driver system 150, which includes, among others, Gx, Gy and Gz amplifiers. Each Gx, Gy and Gz gradient amplifier excites a corresponding gradient coil in the gradient coil assembly 142 to produce magnetic field gradients used for spatially encoding MR signals during a MRI scan. The gradient coil assembly 142 is included within the resonance assembly 140, which also includes a superconducting magnet having superconducting coils 144, which in operation, provides a homogenous longitudinal magnetic field $B_0$ throughout an open cylindrical imaging volume 146 that is enclosed by the resonance assembly 140. The resonance assembly 140 also includes a RF body coil 148 which in operation, provides a transverse magnetic field $B_1$ that is generally perpendicular to $B_0$ throughout the open cylindrical imaging volume 146. The resonance assembly 140 may also include RF surface coils 149 used for imaging different anatomies of a patient undergoing a MRI scan. The RF body coil 148 and RF surface coils 149 may be configured to operate in a transmit and receive mode, transmit mode, or receive mode.

An object or patient 170 undergoing a MRI scan may be positioned within the open cylindrical imaging volume 146 of the resonance assembly 140. The transceiver 135 in the MRI system controller 130 produces RF excitation pulses that are amplified by an RF amplifier 162 and provided to the RF body coil 148 and RF surface coils 149 through a transmit/receive switch (T/R switch) 164.

As mentioned above, RF body coil 148 and RF surface coils 149 may be used to transmit RF excitation pulses and/or to receive resulting MR signals from a patient undergoing a MRI scan. The resulting MR signals emitted by excited nuclei in the patient undergoing a MRI scan may be sensed and received by the RF body coil 148 or RF surface coils 149 and sent back through the T/R switch 164 to a pre-amplifier 166. The amplified MR signals are demodulated, filtered and digitized in the receiver section of the transceiver 135. The T/R switch 164 is controlled by a signal from the pulse generator 133 to electrically connect the RF amplifier 162 to the RF body coil 148 during the transmit mode and connect the pre-amplifier 166 to the RF body coil 148 during the receive mode. The T/R switch 164 may also enable RF surface coils 149 to be used in either the transmit mode or receive mode. The resulting MR signals sensed and received by the RF body coil 148 are digitized by the transceiver 135 and transferred to the memory 137 in the MRI system controller 130.

An MR scan is complete when an array of raw k-space data, corresponding to the received MR signals, has been acquired and stored temporarily in the memory 137 until the data is subsequently transformed to create images. This raw k-space data is rearranged into separate k-space data arrays for each image to be reconstructed, and each of these separate k-space data arrays is input to the array processor 139, which operates to Fourier transform the data into arrays of image data.

The array processor 139 uses a known transformation method, most commonly a Fourier transform, to create images from the received MR signals. These images are communicated to the computer system 120 where they are stored in memory 126. In response to commands received from the operator workstation 110, the image data may be archived in long-term storage or it may be further processed by the image processor 128 and conveyed to the operator workstation 110 for presentation on the display 118.

In various embodiments, the components of computer system 120 and MRI system controller 130 may be implemented on the same computer system or a plurality of computer systems.

Figure 2:
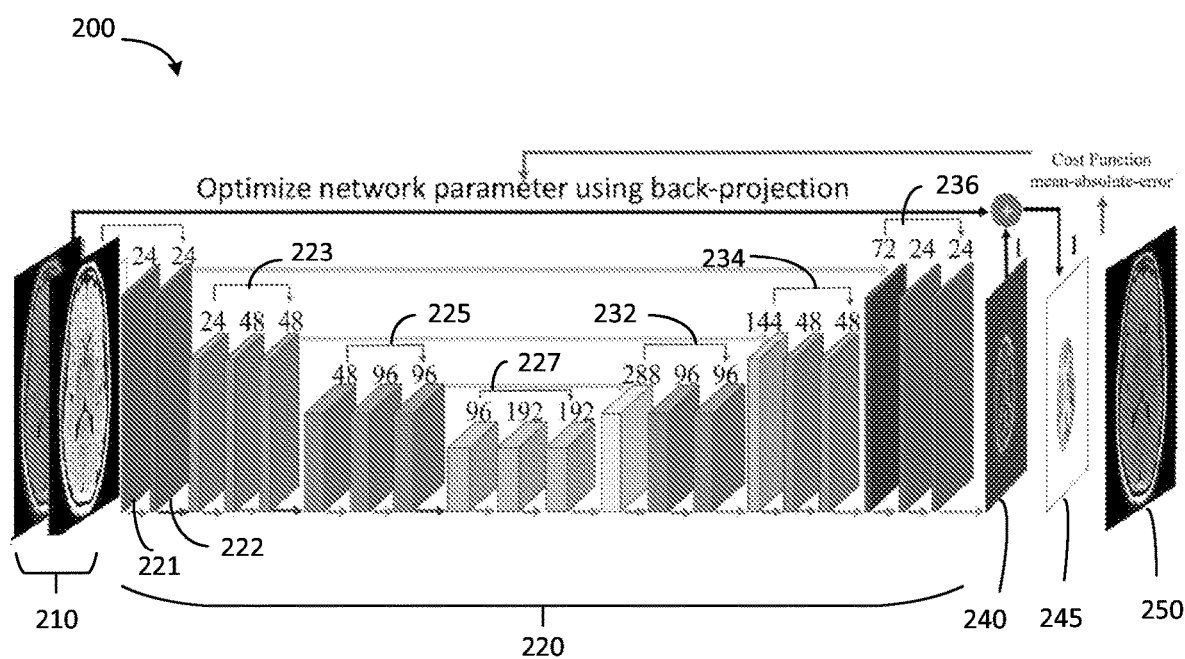
FIG. 2 is a schematic diagram of a system for synthesizing contrast image(s) from a quantitative acquisition, in accordance with an exemplary embodiment.

Referring to FIG. 2, a schematic diagram of a system 200 for synthesizing contrast image(s) from a quantitative acquisition is shown, in accordance with an exemplary embodiment. At the training stage of a deep neural network 220, a quantitative acquisition (e.g., images acquired from a quantification scan) 210 is input to the deep neural network 220, which in turn outputs a synthesized contrast image 240. The synthesized contrast image 240 is compared with a corresponding ground truth contrast image 250 acquired from a contrast scan. The difference (i.e., the loss) 245 is back projected to the deep neural network 220 to optimize (i.e., to train) the network parameters. After being trained (and validated), the deep neural network 220 can be exploited to map a quantitative acquisition to corresponding contrast image(s), using the optimized network parameters. The trained deep neural network 220 may be stored at the imaging device (e.g., memory 126 in FIG. 1), at an edge device connected to the imaging device, a cloud in communication with the imaging device, or any appropriate combination thereof.

Figure 3:
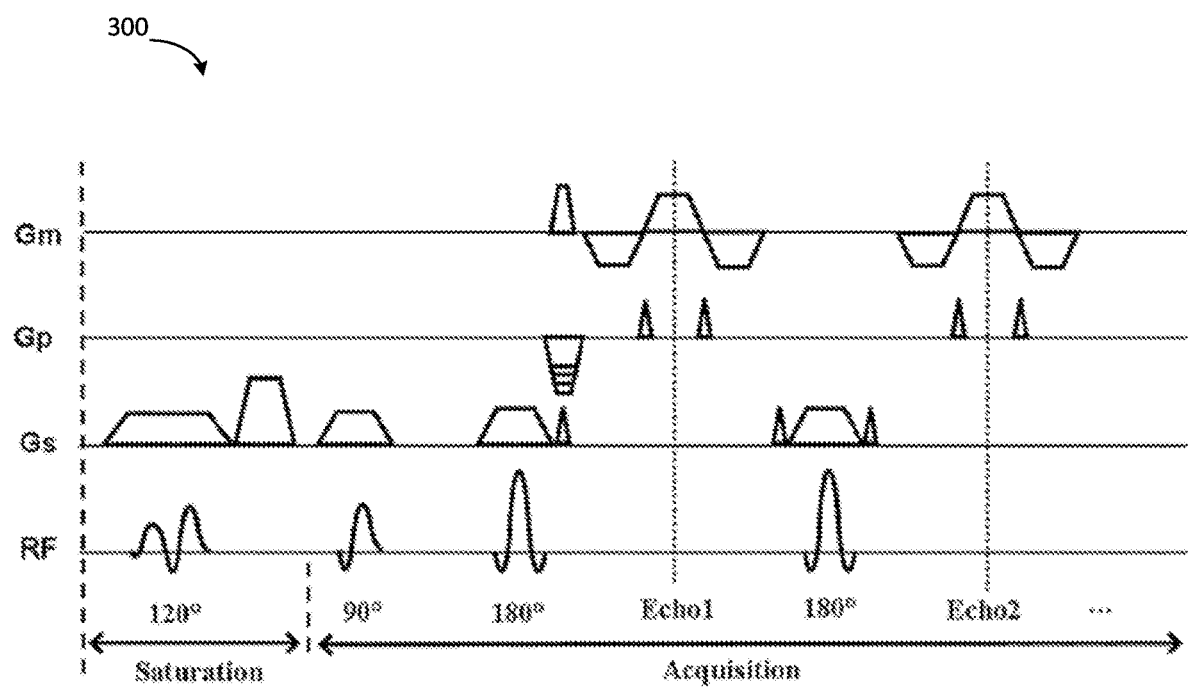
FIG. 3 is a schematic diagram of a single block of a pulse sequence for performing a quantification scan, in accordance with an exemplary embodiment.

Referring to FIG. 3, a schematic diagram of a single block of a pulse sequence 300 for performing a quantification scan is shown, according to an exemplary embodiment. A two-dimensional (2D) fast spin echo (FSE) multi-delay multi-echo (MDME) sequence may be performed for the quantification scan, which includes an interleaved slice selective saturation RF pulse and multi-echo acquisition. The saturation acts on a slice n, whereas the acquisition acts on a slice m, using the 90° excitation pulse and multiple 180° pulses. n and m are different slices. As such, the effective delay time between saturation and acquisition of each particular slice can be varied by the choice of n and m. In some embodiments, four (4) different choices of n and m are performed, resulting in four different delay times. The number of echoes may be set as two (2), at two different echo times. Hence, the result of the quantitative acquisition 210 is eight (8) complex images per slice (although two images are shown in FIG. 1). It should be understood that the example of 4 delays at 2 echoes is described herein for illustration, not for limitation. Any appropriate combination of delays and echoes can be used to perform the quantification scan. It should also be understood that any appropriate quantification sequence besides MDME sequence may be used. Furthermore, the quantitative acquisition 210 may be raw MRI signals in k-space in some embodiments, such as raw MDME MRI.

Referring back to FIG. 2, the deep neural network 220 may be a multi-scale U-Net convolutional neural network (CNN) with an encoder-decoder structure. In the example shown in FIG. 2, an input layer 221 receives the quantitative acquisition 210. In some embodiments, the input layer 221 includes multiple channels to accommodate the input of the multiple images as the result of a quantitative acquisition at once. In some embodiments, each of the multiple images is split up into real and imaginary components and stacked as a corresponding channel. A pooling layer 222 is configured to down-sample the output from the input layer 221.

The output from the pooling layer 222 is passed through three (3) encoder modules (223, 225, and 227) followed by three (3) decoder modules (232, 234, and 236), each module consisting of three (3) convolutional layers. In some embodiments, a down-sampling layer or an up-sampling layer is located at the end of a module for connection to the following module. Each layer is made up of a plurality of "neurons" (also known as "nodes") with trainable weights and biases. Each neuron receives several inputs, takes a weighted sum over them, passes it through an activation function, and responds with an output. In some embodiments, concatenated connections and residual connections are used to accelerate training convergence, improve the reconstruction accuracy, and restore resolution information.

The weights and biases of the convolutional layers in the deep neural network 220 are learned during training. More specifically, a loss function 245 is defined to reflect the difference between the contrast image 240 synthesized by the deep neural network 220 and a corresponding ground truth contrast image 250. The ground truth contrast image 250 may be, for example, T1- or T2-weighted, T1- or T2-FLAIR, proton density-weighted, STIR image, or the like, acquired from a contrast scan. In some embodiments, the loss function 245 is the mean-absolute error, i.e., equal to the mean of absolute difference of pixel values between the ground truth contrast image 250 and the synthesized contrast image 240. In some embodiments, the synthesized contrast image 240 is registered to the ground truth contrast image 250 before the calculation of the loss function 245. Other loss functions may be used, such as root-mean-squared-error (RMSE), structural-similarity-index (SSIM), etc. The loss 245 is then back projected to the deep neural network 220 to update the weights and biases of the convolutional layers. A plurality pairs of quantitative acquisition and corresponding contrast image(s) may be used to train the deep neural network 220. In this example, the deep neural network 220 is trained in an intra-contrast manner. For example, one model is dedicated to a particular contrast type or a separate channel is set up for each contrast type within a model, each model or channel being trained separately.

The deep neural network 220 can be trained to synthesize a T2*-weighted image by using ground truth T2*-weighted images as reference during the training. Generally, T2*-weighted images cannot be synthesized with conventional model-fitting method.

It should be understood that the layout of the neural network 220 as shown in FIG. 2 is for illustration, not for limitation. A different neural network architecture may be used herein for synthesizing contrast image(s) from a quantitative acquisition. For example, different neural network structures may include residual networks (ResNets), auto-encoder, recurrent neural networks, and fully connected networks.

Figure 4:
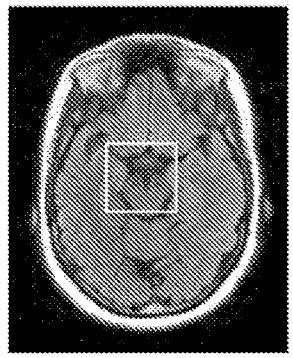
FIG. 4 shows T2-FLAIR images of a brain obtained by various techniques.
Figure 4:
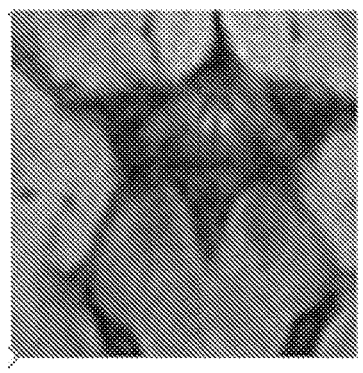
Figure 4:
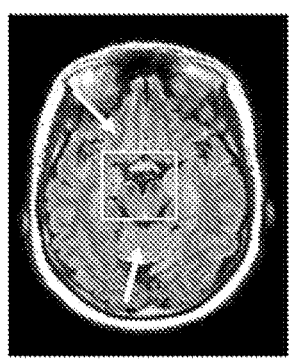
Figure 4:
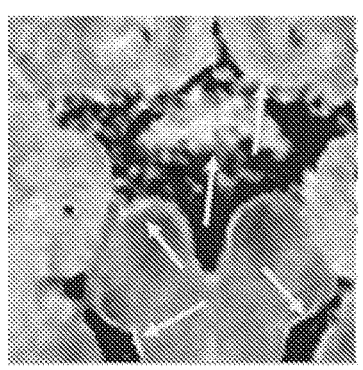
Figure 4:
Figure 4:
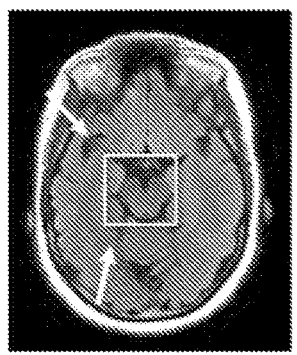
Figure 4:
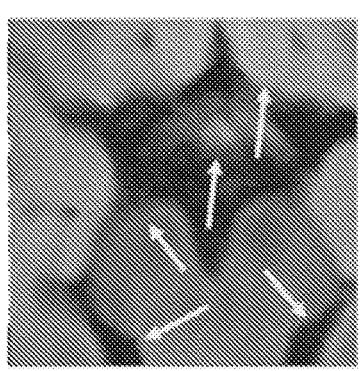
Figure 4:

Referring to FIG. 4, T2-FLAIR images of a brain obtained by various techniques are shown for comparison. The first row shows a ground truth T2-FLAIR image acquired by a contrast scan as the reference image and a zoom-in view of the central region marked in the reference image. The second row shows a T2-FLAIR image synthesized from a MDME acquisition with conventional model-fitting method, a zoom-in view of the central region, and a 5× magnified error map reflecting the error in the central region. The third row shows a T2-FLAIR image synthesized from a MDME acquisition with a trained deep neural network as described above, a zoom-in view of the central region, and a 5× magnified error map reflecting the error in the central region. The MDME acquisition was a 2D FSE based MDME with four (4) saturation delays and two (2) echoes. The deep neural network was trained on around 1900 different datasets, which include paired inputs and outputs at 26-30 planes from 8 subjects with 8 types of data augmentation using rigid transformation to avoid overfitting. Conventional 2D FSE brain images were used as ground truth contrast images. Then the trained neural network was applied to other datasets, and the performance of the trained deep learning model was evaluated based on the result.

T2-FLAIR, as discussed above, is one of the most challenging contrasts to accurately synthesize in clinical studies. Conventional model-fitting method often results in recognizable artifacts which prevent its clinical application. As shown in FIG. 4, the data-driven deep learning approach achieved both improved accuracy and reduced artifacts for synthesizing T2-FLAIR. In particular, the zoom-in views demonstrate that the deep learning approach resolved the fake boundary artifacts which appeared in the model-fitting result. The arrows highlight the reduced boundary artifacts. The error maps demonstrate that the deep learning approach achieved lower errors than the conventional model-fitting method.

In addition, various metrics were used to compare the performance of the deep learning approach with the performance of the conventional model-fitting method, including for example, root-mean-squared-error (RMSE), peak-signal-to-noise-ratio (PSNR), and SSIM. All demonstrated superior performance of the deep learning approach over the model-fitting method. With T2-FLAIR synthesis as an example, the deep learning approach outperformed existing model-fitting based method.

Figure 5:
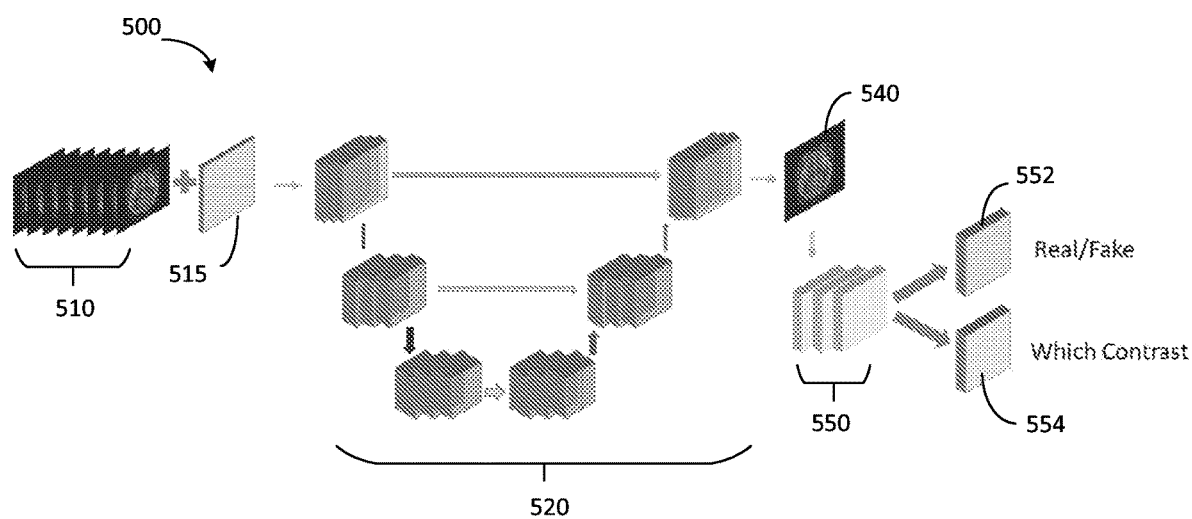
FIG. 5 is a schematic diagram of a system for synthesizing contrast image(s) from a quantitative acquisition, in accordance with another exemplary embodiment.

Referring to FIG. 5, a schematic diagram of a system 500 for synthesizing one or more contrast images from a quantitative acquisition is shown, in accordance with another exemplary embodiment. A quantitative acquisition (e.g., images acquired by a quantification scan) 510 and a target contrast type 515 are input to a deep neural network 520, which in turn outputs a synthesized contrast image 540. The synthesized contrast image 540 is then passed through a discriminator and classifier module 550, which outputs a discriminator 552 and a classifier 554. The discriminator 552 indicates whether the synthesized contrast image 510 is of realistic image quality. If so, the classifier 554 indicates which contrast type the synthesized contrast image 510 is. Different than the system 200 of FIG. 2, in this example, the deep neural network 520 is trained in an inter-contrast manner. For example, one set of network parameters is trained on and applied to multiple contrast types. Thus, correlation between different contrast types is utilized to reach a mutual correction effect.

Like the quantitative acquisition 210 in FIG. 2 as discussed above, the quantitative acquisition 510 may be multiple complex images reconstructed from MR signals acquired by an MDME sequence. The target contrast type 515 may be identified by an operator (e.g., a radiologist). In some embodiments, a mask vector is used to indicate the target contrast type, using "1" for the desired contrast type in the vector while using "0" for the others.

Like the deep neural network 220 in FIG. 2 as discussed above, the deep neural network 520 may be a U-Net CNN with an encoder-decoder structure. In some embodiments, concatenated connections and residual connections are used to accelerate training convergence, improve the reconstruction accuracy, and restore resolution information. The weights and biases of the convolutional layers are learned during training.

The discriminator and classifier module 550 may be another CNN including multiple convolutional layers. The module 550 is configured to determine whether an image has realistic quality and if so, which contrast type the image is. In some embodiments, two separate modules may be used as the discriminator and the classifier, respectively. In operation, the discriminator and classifier module 550 may be trained by a plurality of datasets. The training datasets may include realistic images of all types (T1- and T2-weighted, T1- and T2-FLAIR, proton density weighted, STIR, etc.) and synthesized images not of realistic quality. Each image may be labeled as real or fake. For images of realistic quality, the contrast type can be further labeled. After the discriminator and classifier module 550 is trained, it may be connected to the deep neural network 520 to help train the network 520.

Figure 6:
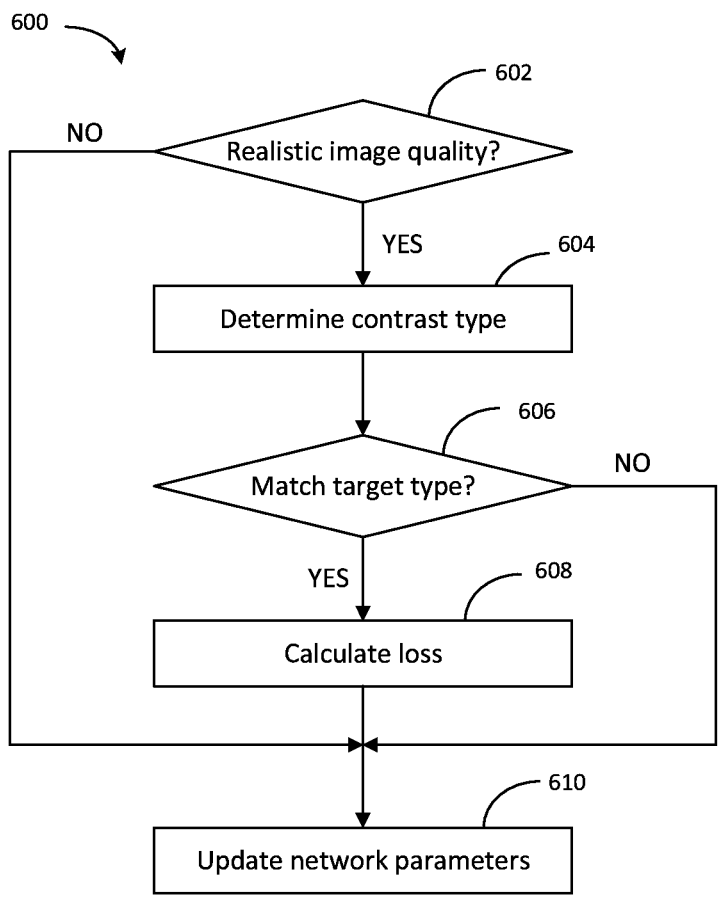
FIG. 6 is a flow chart of a method for training the deep neural network used in the system of FIG. 5, in accordance with an exemplary embodiment.

Referring to FIG. 6, a flow chart 600 of a method for training the deep neural network 520 is shown, in accordance with an exemplary embodiment. The datasets for training the network 520 may include a plurality pairs of quantitative acquisition and corresponding ground truth contrast images acquired from contrast scans as references. In some embodiments, the training process can handle situations where different datasets have different subsets of references. For each ground truth contrast image, the contrast type is labeled. Target contrast types(s) may be input to the deep neural network 520 with the quantitative acquisition 510. Based on the quantitative acquisition 510 and the target contrast type 515, the deep neural network 520 produces the synthesized contrast image 540, which is passed to the discriminator and classifier module 550.

At 602, the discriminator and classifier module 550 decides whether the image 540 has realistic image quality. If the discriminator 552 indicates "NO," this indication is then back projected to the deep neural network 520 to update the network parameters, at operation 610. If the discriminator indicates "YES," the method proceeds to 604, where the discriminator and classifier module 550 decides which contrast type 554 the synthesized image 540 is. At 606, it is determined whether the contrast type 554 matches the target contrast type 515. If it is "NO" at operation 606, this indication is then back projected to the deep neural network 520 to update the network parameters, at operation 610. If it is "YES" at operation 606, the method proceeds to 608, where a loss is calculated. The loss may be any appropriate function reflecting the difference between the synthesized image 540 and the corresponding ground truth contrast image of the same type. The loss is then back projected to the deep neural network 520 to adjust the network parameters, at 610. After being trained (and validated), the deep neural network 220 can be exploited to map a quantitative acquisition to corresponding contrast image(s) of any target type, using the optimized network parameters.

The method 600 may be repeated a plurality of times to train the deep neural network 520. As such, one set of network parameters is trained on and applied to multiple contrast types. After training and validation, the deep neural network 520 may be used to synthesize any type of contrast images identified by the operator.

Figure 7:
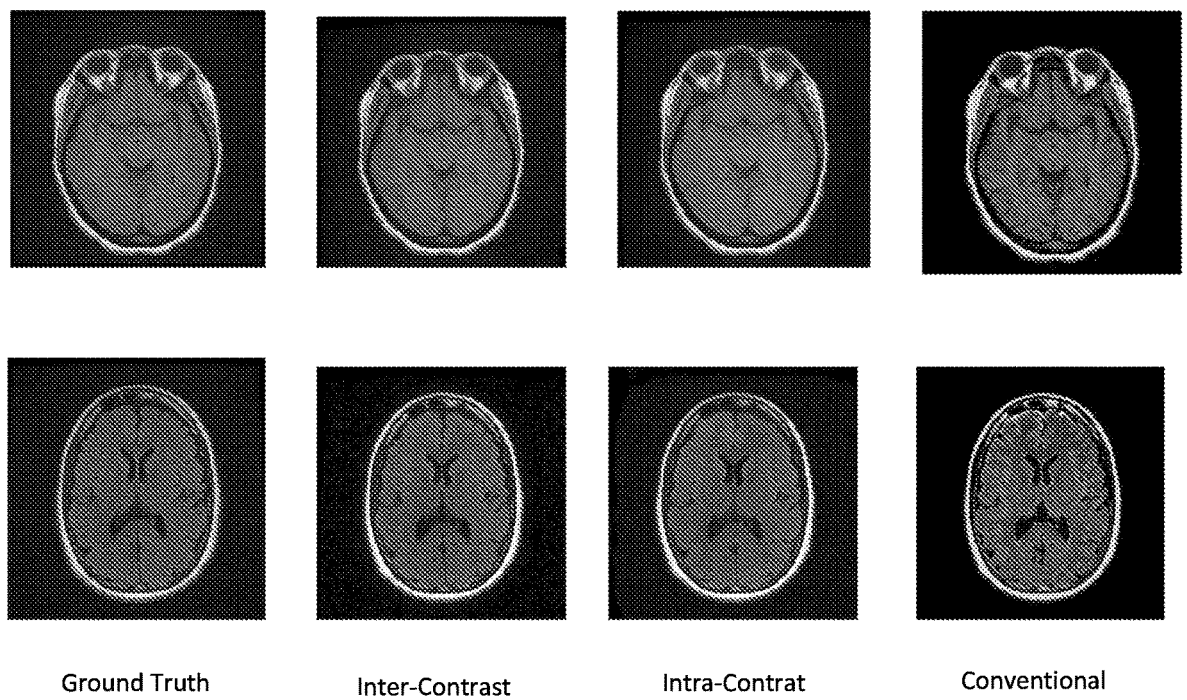
FIG. 7 shows T1-weighted and T2-FLAIR images of a brain obtained by various techniques.

Referring to FIG. 7, T1-weighted and T2-FLAIR images of a brain obtained by various techniques are shown. The first column shows ground truth images acquired by contrast scans as references, T1-weighted image at the top and T2-FLAIR image at the bottom. The second column shows synthesized images by inter-contrast deep learning approach (e.g., the method described above with reference to FIGS. 5 and 6). The third column shows synthesized images by intra-contrast deep learning approach (e.g., the method described above with reference to FIG. 2). The fourth column shows synthesized images by conventional model-fitting method. The inter-contrast synthesized images are shown to be the closest to the ground truth images because the convolutions share information between all channels, allowing them to exploit correlations between the multiple contrast types of images on a data-driven basis.

Figure 8:
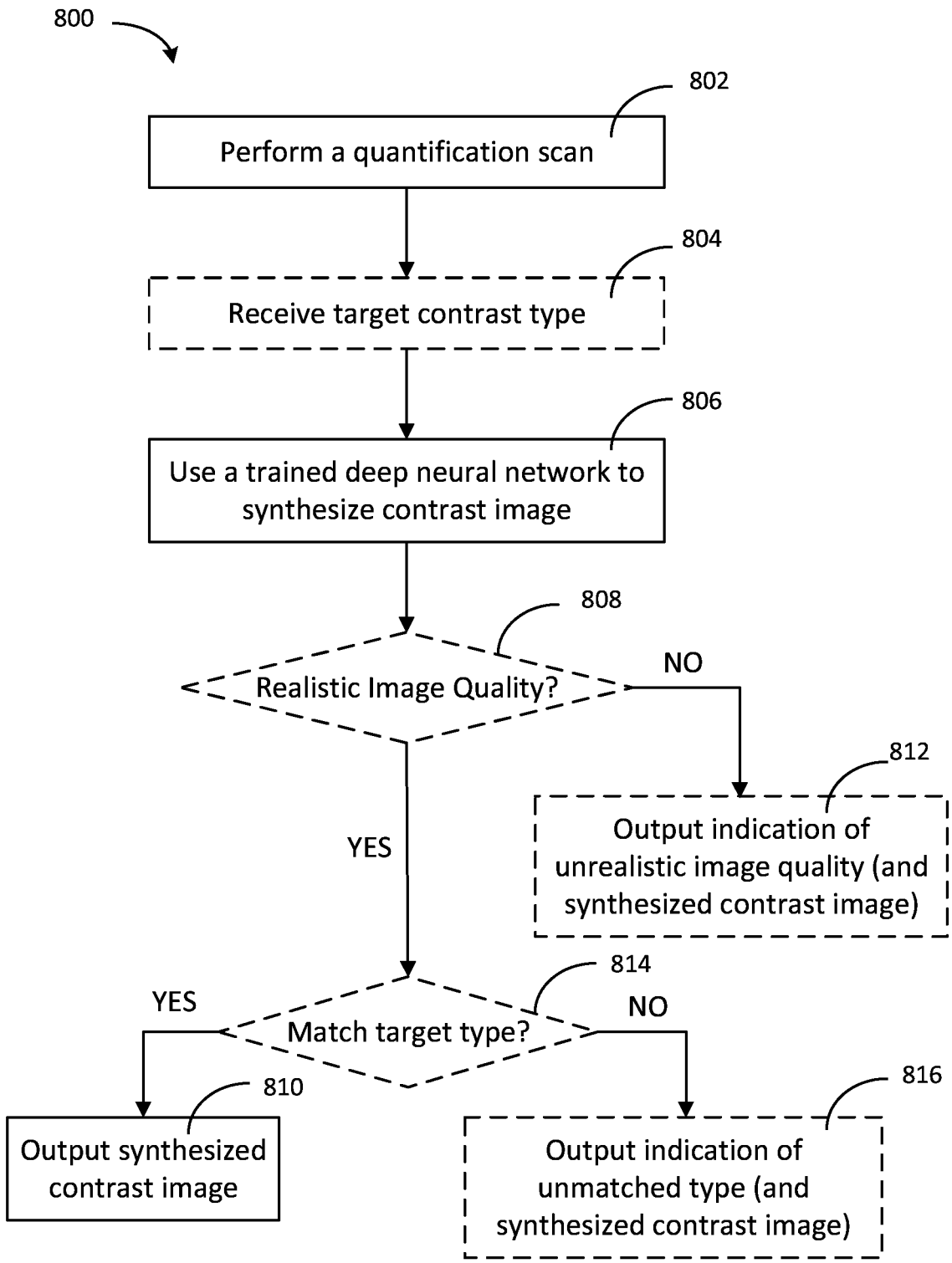
FIG. 8 is a flow chart of a method for synthesizing contrast image(s) from a quantification acquisition, in accordance with an exemplary embodiment.

Referring to FIG. 8, a flow chart of a method 800 for synthesizing contrast image(s) from a quantification acquisition is shown, in accordance with an exemplary embodiment. At 802, a quantification scan is performed by an MRI system, for example, the MRI system 100 in FIG. 1. As used herein, a "quantification scan" refers to the measurement of MR signals reflecting absolute values of physical parameters of tissues being scanned. In some embodiments, an MDME sequence may be used to perform the quantification scan. Any other appropriate quantification sequences may be used to perform the quantification scan.

At an optional operation 804, the target contrast type identified by an operator is received. This operation is not needed for the intra-contrast method, but may be included in the inter-contrast method. The operator may determine which target contrast type is desired.

At an operation 806, a trained deep neural network is used to synthesize a contrast image from the quantitative acquisition, based on the target contrast type if applicable. As used herein, the quantitative acquisition refers to MR signals acquired by the quantification scan. In some embodiments, the quantitative acquisition may be the raw MRI signals in k-space. In some embodiments, the quantitative acquisition may be the reconstructed signals in the image domain. For example, when an MDME with four delay times and two echo times is used to scan, the quantitative acquisition may be eight complex images.

In some embodiments, the deep neural network may be a U-Net CNN with an encoder-decoder structure (e.g., deep neural networks 220 and 520). In some embodiments, a different neural network architecture may be used, such as ResNets, autoencoder, recurrent neural networks, fully connected networks, and so on. The deep neural network has been trained to map the quantitative acquisition to one or more contrast types of images. For example, the weights and biases of the convolutional layers of the deep neural network have been optimized based on training datasets. In some embodiments, a plurality pairs of quantitative acquisition and corresponding ground truth contrast image(s) acquired by contrast scans may be used to train the deep neural network. In some embodiments where the inter-contrast approach is implemented, the deep neural network may be trained in accordance with the method 600 described above with reference to FIG. 6.

In some embodiments, the contrast image synthesized by the trained neural network may then be output, at operation 810. The contrast type may include, for example, T1- and T2-weighted, T1- and T2-FLAIR, proton density-weighted, and STIR images. In some embodiments, the contrast type may be one that cannot be synthesized by the conventional pixel-by-pixel (or voxel-by-voxel) model fitting method, for example, the T2*-weighted image.

In some embodiments where a discriminator (e.g., as shown in FIG. 5) is used, the discriminator may decide whether the synthesized image is of the realistic image quality, at operation 808. In some embodiments, the discriminator is CNN with multiple convolutional layers trained to distinguish images of realistic image quality from those of fake image quality. If the synthesized image does not have realistic image quality (i.e., "NO" at 808), the indication of fake image quality may be output at operation 812. In some embodiments, the synthesized image may be output along with the indication. If the synthesized image has realistic image quality (i.e., "YES" at 808), a classifier (e.g., as shown in FIG. 5) may decide whether the type of the synthesized contrast image matches the target contrast type, at operation 814. If the types do not match (i.e., "NO" at 814), such indication may be output at operation 810. In some embodiments, the synthesized image may be output along with the indication. If the types match (i.e., "YES" at 814), the synthesized contrast image is output at 810.

With the systems and methods described above, synthetic MRI with data-drive deep learning approach can outperform conventional pixel-by-pixel (or voxel-by-voxel) model-fitting method with improved accuracy and reduced artifacts.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Further, it is to be understood that embodiments of the present invention may be applicable to traditional MRI, UTE MRI, Silent MRI, PET/MRI, multispectral/hyperspectral imaging, multi-energy CT, multi-tracer PET, and/or any type of MRI based imaging system with appropriate adjustment. Further still, as will be appreciated, embodiments of the present invention related imaging systems may be used to analyze tissue generally and are not limited to human tissue. Also, as used herein, the examples and embodiments, in all respects, are meant to be illustrative only and should not be construed to be limiting in any manner.

What is claimed is:

1. A method for synthesizing a magnetic resonance (MR) contrast image, the method comprising:

performing a quantification scan, wherein the quantification scan is the measurement of MR signals reflecting absolute values of physical parameters of tissues being scanned;

using a trained deep neural network to synthesize the MR contrast image from a quantitative acquisition obtained by the quantification scan;

outputting the MR contrast image synthesized by the trained deep neural network; and wherein the quantification scan is the input to the trained deep neural network.

2. The method of claim 1, wherein performing the quantification scan comprises acquiring MR signals with a multi-delay multi-echo (MDME) sequence.

3. The method of claim 1, wherein the quantitative acquisition is multiple complex images reconstructed from MR signals acquired by the quantification scan.

4. The method of claim 1, wherein the MR contrast image synthesized by the trained deep neural network is one of T1-weighted image, T-2 weighted image, T1-FLAIR image, T2-FLAIR image, proton density weighted image, and STIR image.

5. The method of claim 1, wherein the MR contrast image synthesized by the trained deep neural network is a T2*-weighted image.

6. The method of claim 1, further comprising:

receiving, at the trained deep neural network, a target contrast type for the synthesized MR contrast image.

7. The method of claim 6, further comprising:

using a trained discriminator to determine whether the synthesized MR contrast image is of realistic image quality; and in response to determining that the synthesized MR contrast image is not of realistic image quality, outputting an indication to indicate that.

8. The method of claim 6, further comprising:

using a trained classifier to determine the contrast type of the synthesized MR contrast image;

determining whether the determined contrast type matches the target contrast type; and in response to determining that the determined contrast type does not match the target contrast type, outputting an indication to indicate that.

9. A magnetic resonance imaging (MRI) system comprising:

a gradient coil assembly configured to generate gradient magnetic fields;

a radio frequency (RF) coil assembly configured to generate RF pulses;

a display;

a controller in communication with the gradient coil assembly, the RF coil assembly, and the display and configured to:

instruct the gradient coil assembly and RF assembly to generate a sequence to perform a quantification scan, wherein the quantification scan is the measurement of MR signals reflecting absolute values of physical parameters of tissues being scanned;

instruct a trained deep neural network to synthesize a MR contrast image from a quantitative acquisition obtained by the quantification scan;

output the MR contrast image synthesized by the trained deep neural network at the display; and wherein the quantification scan is the input to the trained deep neural network.

10. The MRI system of claim 9, wherein the sequence for the quantification scan is an MDME sequence.

11. The MRI system of claim 9, wherein the target contrast type is any of T1-weighted, T2-weighted, T2*-weighted image, T1-FLAIR, T2-FLAIR, proton density weighted, and STIR.

12. The MRI system of claim 9, further comprising a memory storing the trained deep neural network.

13. The MRI system of claim 12, wherein the trained deep neural network is a multi-scale U-Net convolutional neural network (CNN) with an encoder-decoder structure.

14. A method for synthesizing a magnetic resonance (MR) contrast image, the method comprising:
  performing a quantification scan, wherein the quantification scan is the measurement of MR signals reflecting absolute values of physical parameters of tissues being scanned;
  receiving a target contrast type;
  using a trained deep neural network to synthesize the MR contrast image from a quantitative acquisition obtained by the quantification scan based on the target contrast type;
  using a trained discriminator to determine whether the synthesized MR contrast image is of realistic image quality;
  in response to determining that the synthesized MR contrast image is of realistic image quality, using a trained classifier to determine the contrast type of the synthesized MR contrast image;
  determining whether the determined contrast type matches the target contrast type;
  in response to determining that the determined contrast type matches the target contrast type, outputting the synthesized image; and
  wherein the quantification scan is the input to the trained deep neural network.

15. The method of claim 14, further comprising:
  in response to determining that the synthesized MR contrast image is not of realistic image quality, outputting an indication to indicate that.

16. The method of claim 14, further comprising:
  in response to determining that the determined contrast type does not match the target contrast type, outputting an indication to indicate that.

17. The method of claim 14, wherein the target contrast type is any of T1-weighted, T2-weighted, T2*-weighted image, T1-FLAIR, T2-FLAIR, proton density weighted, and STIR.

18. The method of claim 17, wherein the trained deep neural network uses one set of parameters for all contrast types.

* * * * *